United States Patent [19]

Shimada et al.

[11] 4,385,274

[45] May 24, 1983

[54] METHOD AND DEVICE FOR COMPENSATING TEMPERATURE-DEPENDENT CHARACTERISTIC CHANGE IN ION-SENSITIVE FET TRANSDUCER

[75] Inventors: Kiyoo Shimada; Hayami Yoshimochi; Makoto Yano; Kyoichiro Shibatani, all of Kurashiki, Japan

[73] Assignee: Kuraray Co., Ltd., Okayama, Japan

[21] Appl. No.: 257,605

[22] Filed: Apr. 27, 1981

[30] Foreign Application Priority Data

Apr. 28, 1980 [JP] Japan .................................. 55-56901
Jun. 12, 1980 [JP] Japan .................................. 55-79703

[51] Int. Cl.³ ............................................. G01N 27/00
[52] U.S. Cl. ..................................... 324/71.6; 357/25; 204/416
[58] Field of Search ................ 324/425, 71 SN, 71 R; 357/25; 204/195 M

[56] References Cited

U.S. PATENT DOCUMENTS 4,269,682 5/1981 Yano et al. ............................. 357/25

Primary Examiner—Michael J. Tokar
Assistant Examiner—Kevin D. O'Shea
Attorney, Agent, or Firm—Birch, Stewart, Kolasch and Birch

[57] ABSTRACT

An electrical circuitry for use in the measurement of the activity of ions in an electrolyte solution carried out by the use of an ion-sensitive field-effect transistor transducer having a gate or ion sensitive layer, a source and a drain. The measurement is carried out by adjusting the drain current flowing through the field-effect transistor to a predetermined value such that the temperature dependency of the electroconductivity of the channel of the transistor becomes equal to the sum of the temperature dependency of the potential at an interface between a reference electrode and the electrolyte solution and the temperature dependency of the potential at an interface between the ion-sensitive layer and the electrolyte solution.

6 Claims, 14 Drawing Figures

METHOD AND DEVICE FOR COMPENSATING TEMPERATURE-DEPENDENT CHARACTERISTIC CHANGE IN ION-SENSITIVE FET TRANSDUCER

BACKGROUND OF THE INVENTION

The present invention generally relates to the utilization of an ion-sensitive field-effect transistor (FET) and, more particularly, to a method and device for compensating variation in characteristic of an ion-sensitive FET transducer which would result from change in temperature.

As an instrument for the measurement of ion activities in electrochemical and biological environments, an ion-sensitive electrode probe, or an ion sensor as it is generally called, has heretofore been largely employed. An ion-sensitive glass electrode used in most pH detecting devices is a typical ion-sensitive electrode probe. When in use, the ion sensor is directly immersed in a liquid of interest of which the ion activity is desired to be measured, and the measurement of the ion activity can be carried out merely by detecting a potential difference between the ion sensor and a reference electrode. With this ion sensor, a continuous measurement of the ion activity may also be possible. In view of this, the ion sensor is useful and has many applications particularly in a medical field.

However, when it comes to the manufacture of the ion sensor in such a compact and miniature size that it can be used in the measurement, and continuous monitoring of the measurement, of the ion activity in a local area of a tissue of a living body, an output impedance of the glass electrode tends to increase to such an extent that an electrical insulation can hardly be attained with a retarded responsivity.

In order to obviate the above described problem, an ion-sensitive FET transducer comprising a combination of an ion-sensitive electrode and a metal oxide semiconductor field-effect transistor (MOSFET) which serves as a preamplifier has recently been developed. The principle of this ion-sensitive FET transducer and its application for the measurement of the ion activity in a liquid of interest, for example, an electrolyte, are respectively illustrated in FIGS. 1 and 2 of the accompanying drawings, reference to which will now be made for the discussion of the prior art.

Referring first to FIG. 1, the ion-sensitive FET transducer 1 shown therein is of a construction wherein a gate insulating layer 2 is, in place of the gate metal, formed on a channel 5 defined between a source 3 and a drain 4. When in use in the measurement of the ion activity in the electrolyte 6 using a drain-grounded circuit shown in FIG. 2, the potential at the interface between the surface of the gate insulating layer 2 and the surface of the electrolyte 6 varies depending on the activity of a particular ion in the electrolyte 6, as is the case with the potential at the interface between the surface of the glass electrode and the electrolyte. Accordingly, if the potential of the electrolyte 6 is made fixed by using a reference electrode 7, change in potential at the interface between the gate insulating layer 2 and the electrolyte 6 results in change in electroconductivity of the channel 5 situated immediately below the gate insulating layer 2. Therefore, when the measurement of the ion activity is carried out by detecting the potential at the interface between the surface of the gate insulating layer and the surface of the electrolyte in the manner described above, unlike that with the use of the glass electrode, the electrode resistance can be neglected on the one hand and, on the other hand, since the output impedance of the FET is low, such an amplifier of high input resistance as heretofore required in electrical connection with the glass electrode is no longer needed.

The ion-sensitive FET transducer referred to above has the following features.

(1) Since the electrode resistance can be neglected, its miniaturization in size is facilated and, the responsivity in measurement system is high.

(2) Since any existing IC technology can be used in the manufacture of the ion-sensitive FET transducer, various ion sensors can be integrated in a compact size.

(3) The gate insulating layer 2 can be made in a multilayered structure and the layer thickness can be controlled precisely within 100 Å. In other words, since the selectivity of the ion-sensitive FET transducer to ions in the electrolyte is determined by the composition of the surface of the gate insulating layer 2, various types of sensors selectively sensitive to ions can be manufactured merely by suitably selecting the composition of the gate insulating layer 2 which is a layer sensitive to ions. With this ion-sensitive FET transducer, the potential at the interface between the gate insulating layer and the electrolyte or any other liquid of interest is governed by the electrochemical equilibrium as is the case with a usual ion sensitive electrode selectively sensitive to ions.

This ion-sensitive FET transducer described above was first disclosed by Piet Bergveld, IEEE Transactions of Biomedical Engineering, 1970, (Vol. BME 17) and does not make use of the reference electrode during the measurement. However, subsequent to the publication of the ion-sensitive FET transducer by Piet Bergveld, IEEE Transactions of Biomedical Engineering, 1978, (Vol. BME 25) discloses a system of measurement using a combination of the ion-sensitive FET transducer with the reference electrode devised by Matsuo, et al. At the same time, this paper discloses that an ion-sensitive FET transducer of a construction wherein the gate insulating layer is made of silicon nitride ($Si_3N_4$) exhibits an ion selectivity similar to or as comparable to the glass electrode for the pH measurement.

Since then, various attempts have been made to develop improved versions of the ion-sensitive FET transducer including those selectively sensitive to $H^+$, $Na^+$, $K^+$, $Ca^{++}$, $\div Ag^+$, $Cl^-$, $F^-$ and other ions, and even research is nowaday conducted to develop an ion-sensitive FET transducer selectively sensitive to hydrogen gas.

Where the ion activity measurement is to be performed by the use of the ion-sensitive FET transducer, the ion-sensitive FET transducer 1 is, as shown in FIG. 2, immersed in the electrolyte solution 6 contained in a vessel or container 8 with the drain 4 and the source 3 electrically connected respectively to a constant voltage source $+V_d$ and a constant current supply device 9. The constant current supply device 9 is so adjusted that the drain current $I_d$ can always be fixed. During the measurement, the voltage V indicated by a potentiometer 10 is expressed as follows.

$$V = E_g + E_s - E_r \tag{1}$$

wherein Eg, Er and Es represent the gate potential of the ion-sensitive FET transducer 1, the electrode potential of the reference electrode 7 and the potential of the source 3 relatively to the gate, respectively.

Since the potentials Eg and Er tend to be affected by change in temperature and the magnitude of change in characteristic as result of change in temperature varies from one ion-sensitive FET transducer to another, an accurate and precise measurement of the ion activity in the electrolyte solution 6 tends to be hampered.

This will be discussed in more detail. Let it be assumed that the concentration of ions in the electrolyte solution 6 is constant or fixed and that the interface potential of the gate insulating layer 2 relative to the electrolyte solution 6 is expressed by Eg, the potential of the source 3 relative to the gate is expressed by Es, and the potential of the reference electrode 7 relative to the electrolyte solution 6 is expressed by Er. Since the characteristic of the gate insulating layer 2 varies depending on change in temperature T, the potential Eg changes in an amount expressed by $\partial Eg/\partial T$. In addition, since the electroconductivity of the electroconductive channel 5 in the field-effect transistor varies according to the operating current Id flowing from the drain to the source, the source potential Es is also affected by the temperature T, the amount of variation of the source potential Es as a result of change in temperature T being expressed by $\partial Es/\partial T$. Moreover, a similar description applies to the interface potential Er of the reference electrode 7 and the interface potential Er varies according to change in temperature T in an amount expressed by $\partial Er/\partial T$.

Accordingly, when variation in characteristic of the ion-sensitive FET transducer as a result of change in temperature is taken into consideration in the equation (1), the following equation can be obtained.

$$\partial V/\partial T = \partial Eg/\partial T + \partial Es/\partial T - \partial Er/\partial T \quad (2)$$

The amount of variation of the electroconductivity of the channel as a result of change in temperature, i.e., $\partial Es/\partial T$, varies also depending on the type of transducer and/or the method for the manufacture of the transducer. However, the amount of variation of the interface potential of the gate insulating layer 2 as a result of change in temperature i.e., $\partial Eg/\partial T$, corresponds to the term for temperature in the Nernst's equation. On the other hand, the temperature dependency of the interface potential of the reference electrode is discussed in details in, for example, Kagaku Binran, Kiso-hen II (Manual of Chemistry, Fundamental II), #9.9 Cell, 1966, edited by the Chemical Society of Japan, and is described as dependent on the material for the electrode and the concentration of ions in the solution contained therein. However, even if the material for the electrode and the concentration of ions in the solution are both fixed, the electroconductivity still varies depending on the method of the manufacture of the transducer to some extent.

In view of the fact that the transducer composed of the various elements each having its own characteristic variable depending on change in temperature has heretofore been used in the measurement of the ion activity, not only an accurate and precise measurement can hardly be achieved, but also compensation for variation in characteristic of the ion-sensitive FET transducer as a whole resulting from change in temperature cannot be achieved easily.

In order to obviate the above described disadvantage and inconvenience, the present inventors have tried the development of the ion-sensitive FET transducer wherein a diode is incorporated therein, taking advantage of the diode which is known as having a substantially fixed temperature dependency. During the measurement carried out by the use of the transducer or FET sensor wherein the diode is incorporated therein, the temperature measurement of the measurement system by the use of the diode as a temperature sensor is carried out at the same time so that, by using a value representative of the temperature dependency of the system including the FET sensor and the reference electrode which has previously been determined, an electric circuitry for the system is devised so as to achieve the compensation for variation in characteristic of the system. However, it has been found that various disadvantages described below are involved.

(a) Since the pattern for the FET manufacturing is complicated, the element tends to become bulky.
(b) The number of lead wirings is increased.
(c) Since the electric circuitry for the system must have a temperature detecting circuit, the electric circuitry for the sensor system tends to become complicated.

Moreover, although the temperature dependency of the diode can be controlled more easily than that of the field-effect transistor, errors tend to occur in the measurement because of different performance characteristics. In order for the error in the measurement to be negligible, not only must the diode be of high quality as compared with that generally used in electronic circuitries, but also the temperature dependency of the measurement system at the operating current for the FET sensor must be controlled to a very small value. By way of example, in the case where the temperature dependency of the measurement system at a certain operating current is 1 mV/°C., while the temperature dependency of the diode is generally permitted within 0.15 mV/°C., the pH measurement at ambient temperature and that at the body temperature will give a maximum difference of about 0.03.

In view of the above, in order to give a precise and accurate measurement according to the method described above, the measurement method requires a strict quality control, which is generally considered hard to achieve, and the employment of the unnecessarily complicated electric measuring circuitry.

SUMMARY OF THE INVENTION

Accordingly, the present invention has been developed with a view to substantially eliminating the disadvantages and inconveniences inherent in the prior art and has for its essential object to provide a method for compensating variation in characteristic of an ion-sensitive FET transducer which would result from change in temperature, which method is effective to measure accurately the concentration of ions without being adversely affected by change in temperature.

It is also an important object of the present invention to provide an improved device for compensating variation in characteristic of the ion-sensitive FET transducer which would result from change in temperature, which device utilizes a simplified and compact electrical circuitry effective to achieve the accurate measurement of the concentration of ions without being adversely affected by change in temperature.

According to the present invention, the measurement is carried out so as to achieve the following relationship in the equation (2) referred to hereinbefore, $$\partial Eg/\partial T + \partial Es/\partial T - \partial Er/\partial T = 0 \qquad (3)$$

so that the measurement of the concentration of ions can be achieved without being adversely affected by change in temperature.

In the equation (3) above, as shown in the graph of FIG. 3, the temperature dependency $\partial Eg/\partial T$ of the interface potential of the gate insulating layer, that is, the ion-sensitive layer, has no concern with the operating current Id flowing between the source-and-drain path and is, therefore, fixed. In addition, the temperature dependency $\partial Er/\partial T$ of the interface potential of the reference electrode is similarly fixed.

On the contrary thereto, the electroconductivity of the channel in the ion-sensitive FET transducer exhibits a temperature dependency which varies in dependence on the operating current Id flowing through the source-and-drain path, and because of this the temperature dependency $\partial Es/\partial T$ of the source potential varies in a manner as shown in the graph of FIG. 3.

In FIG. 3, if the operating current Id is fixed at, for example, $I_T$, the following relationships will be established.

$$\partial Es/\partial T = a, \ \partial Er/\partial T = b, \ \partial Eg/\partial T = c \qquad (4)$$

By combining the equations (3) and (4), the following relationship can be obtained.

$$a + c - b = 0 \qquad (5)$$

In other words, if the drain current Id is adjusted to a certain value, the sum of the values a and c becomes equal to the value b, that is, the temperature dependencies of the respective three elements are counterbalanced with each other. Such certain value of the drain current Id will hereinafter referred to as a cancelling current $I_T$. In the case where the curve is deviated towards either the negative side or the positive side, it is difficult, or even impossible, to find the cancelling current $I_T$. However, since the cancelling current $I_T$ may have a relatively large range of tolerance, the present-day semiconductor manufacturing technology affords an easy control of the performance to an appropriate location. By way of example, although the cancelling current $I_T$ may take any value unless it is excessively high or low, in order to enable a continuous measurement to be performed for a prolonged period of time and also in view of the safety factor to protect the living body, the cancelling current $I_T$ is preferred to be within the range of 5 μA to 1 mA and, more preferably, within the range of 20 μA to 600 μA. If it is lower than 20 μA, noises will appear in the measurement system while, if it is higher than 600 μA, not only is a relatively large amount of battery current consumed, but a potential hazard to the living body will also be present in such a way as to cause a fever.

BRIEF DESCRIPTION OF DRAWINGS

These and other features of the present invention will readily be understood from the following description taken in conjunction with preferred embodiments thereof made with reference to the accompanying drawings, in which.

DETAILED DESCRIPTION OF EMBODIMENTS

Figure 1:
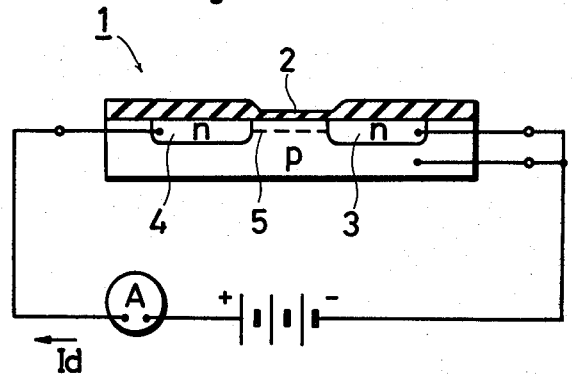
FIG. 1 is a sectional view of the prior art ion-sensitive FET transducer.
Figure 2:
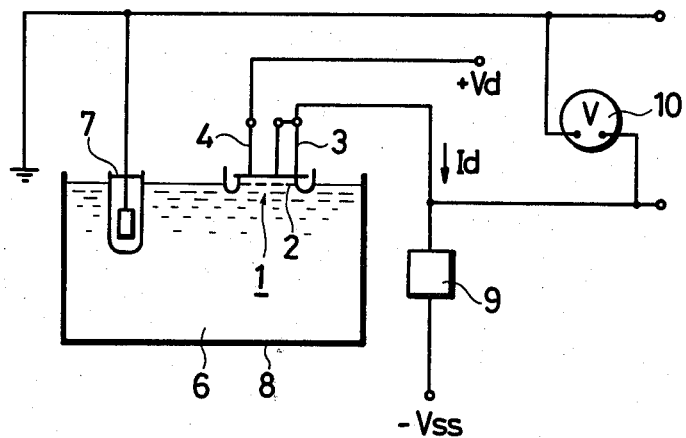
FIG. 2 is an explanatory diagram showing the prior art electrical circuitry used for the measurement of the ion activity.
Figure 3:
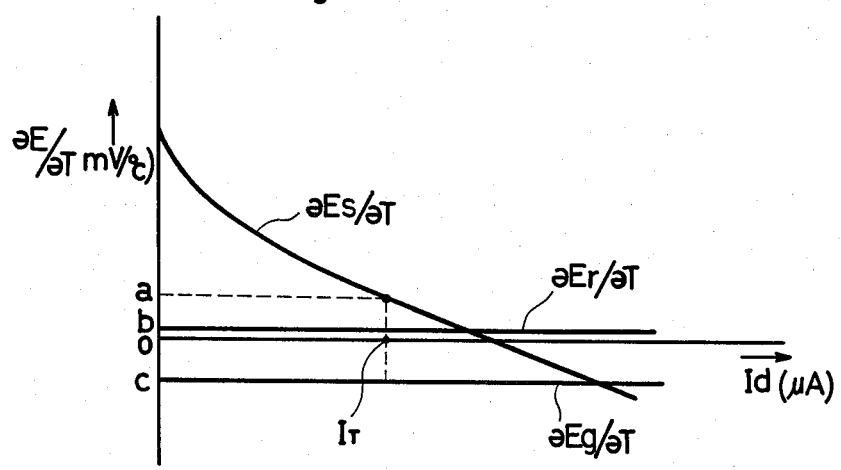
FIG. 3 is a schematic graph showing the characteristic of the temperature compensation during the measurement of the ion activity.

Before the description of the present invention proceeds, it is to be noted that like parts are designated by like reference numerals throughout the accompanying drawings.

Figure 4:
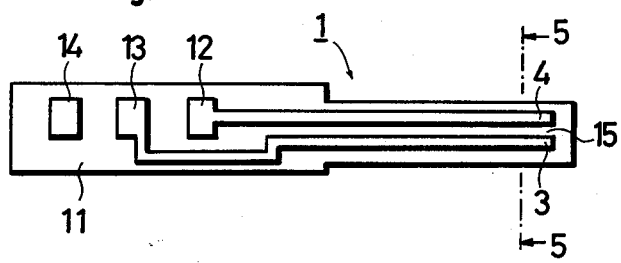
FIG. 4 is a top plain view of the prior art ion-sensitive FET transducer.
Figure 5:
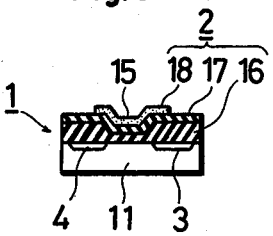
FIG. 5 is a cross sectional view taken along the line 5—5 in FIG. 4.

Referring first to FIGS. 4 and 5, there is shown an ion-sensitive FET transducer 1 of known construction comprising a p-type silicon substrate 11 having formed thereon two diffused n regions which are known as source 3 and drain 4, respectively. Reference numerals 12, 13, and 14 are electrodes connected to and drawn from the drain 4, the source 3 and the silicon substrate 11, respectively. Reference numeral 15 represents a gate region which has a two-layered structure composed of a layer 16 of silicon oxide deposited on the substrate 11 and a layer 17 of silicon nitride overlaying the layer 16 and which is covered by an ion-sensitive layer 18.

Figure 6:
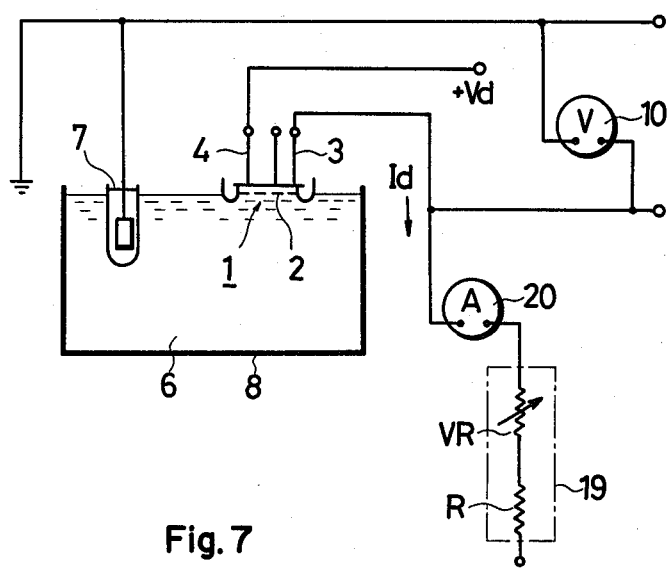
FIG. 6 is a diagram similar to FIG. 2, but according to the present invention.

During the measurement of the ion concentration in the electrolyte solution, as shown in FIG. 6, the source 3 of the ion-sensitive FET transducer 1 is electrically connected to a voltmeter 10 on the one hand and to a current controller 19 composed of a variable resistor VR and a fixed resistor R for controlling the current Id flowing through the source-and-drain path. The circuitry shown in FIG. 6 is so designed that the value of the current Id flowing through source-and-drain path can be indicated by an ammeter 20 inserted between the source 3 and the current controller 19.

Figure 7:
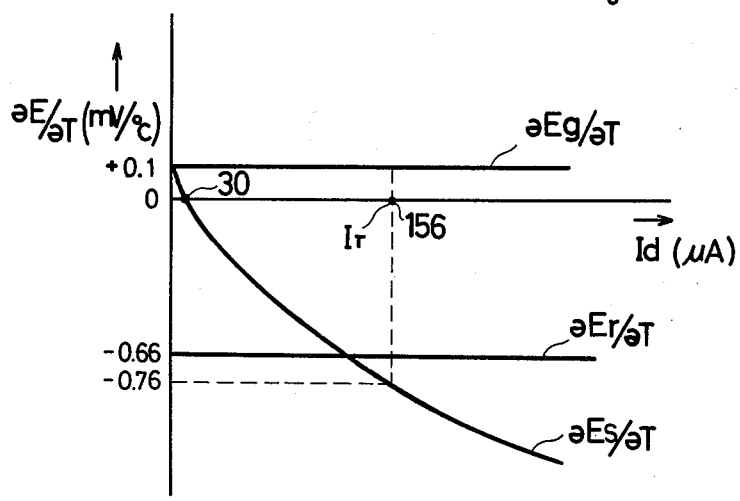
FIG. 7 is an explanatory graph showing the relationships among the temperature dependencies, which is used in connection with the discussion of the present invention.

Referring now to FIG. 7, assuming that the current Id is adjusted to, for example, 156 μA by manipulating the current controller 19 while the indication given by the ammeter 20 is monitored by eye, the following relationships can be established.

$$\partial Eg/\partial T = +0.1 \text{ mV/°C.,}$$

$$\partial Er/\partial T = -0.66 \text{ mV/°C., and}$$

$$\partial Es/\partial T = -0.76 \text{ mV/°C.}$$

Therefore, from the equation (3) referred to hereinbefore, $$+0.1 + (-0.76) - (-0.66) = 0$$

Accordingly, the output voltage indicated by the voltmeter 10 is indicative of the ion concentration and is a measured value of the ion concentration obtained without being adversely affected by change in temperature.

Figure 8:
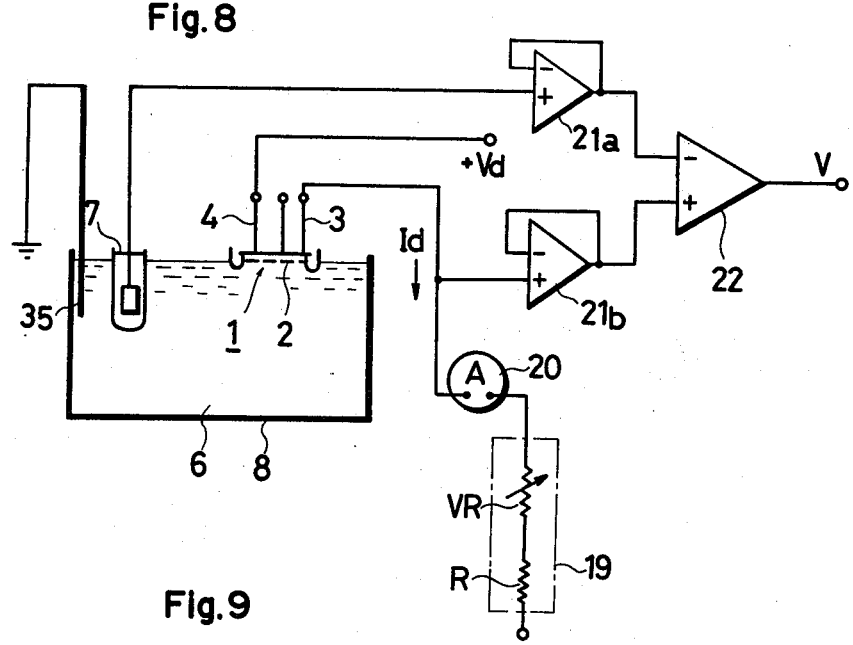
FIG. 8 is a diagram similar to FIG. 2, showing an ion activity measuring circuitry according to another preferred embodiment of the present invention.

The circuitry shown in FIG. 8 is similar to that shown in FIG. 6, except for the difference that the voltmeter 10 used in the circuitry of FIG. 6 is replaced with a combination of a pair of impedance converter 21a and 21b and a subtractor 22. Utilizing a defferential amplifier. With this circuitry shown in FIG. 8, a differential between the sum of the source potential Es and the gate potential Eg and the interface potential Er of the reference electrode 7 can be indicated by an output voltage from the subtractor 22. Even with this ion concentration measuring circuitry shown in FIG. 8, the current Id flowing through the source-and-drain path can be adjusted to the predetermined value $I_T$ by manipulating the current controller 19 while the indication given the ammeter 20 is monitored, as is the case with the circuitry shown in FIG. 6. However, it is to be noted that, in order to keep the potential of the solution 6 at a constant value, a grounded control electrode 35 is immersed in the solution 6.

Figure 9:
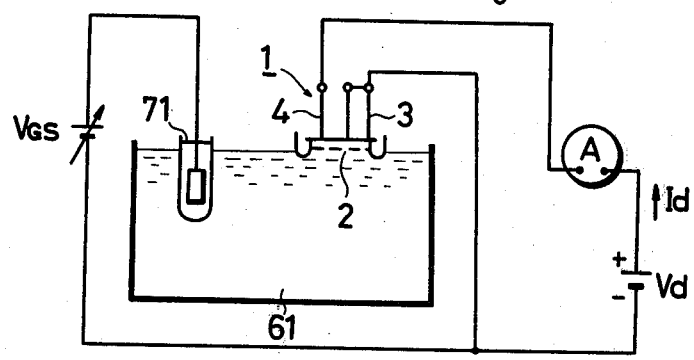
FIG. 9 is a diagram similar to FIG. 2, showing an electric circuitry for the measurement of the cancelling current.

In order to determine a particular value for the cancelling solution $I_T$ to which the current Id flowing through the source-and-drain path during the actual measurement of the ion concentration must be adjusted, an electrical circuit of a construction shown in FIG. 9 is utilized together with the employment of a reference electrode 71 which has a temperature dependency identical with that of the reference electrode 7 actually used during the measurement of the ion concentration.

Figure 10:
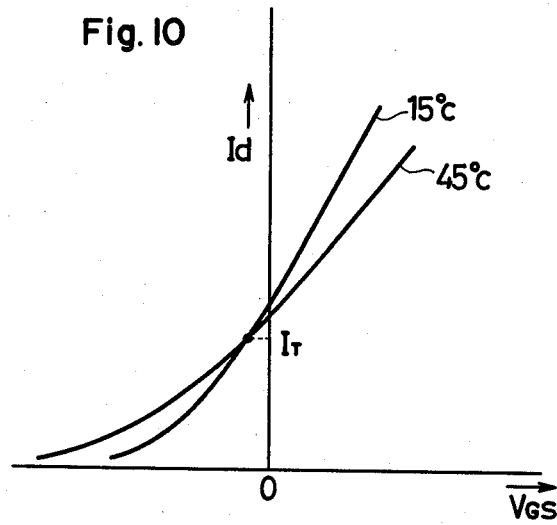
FIG. 10 is a graph showing the relationship between the drain current and the gate-source voltage.

The determination of the cancelling current $I_T$ to which the current Id should be adjusted is carried out by causing the reference electrode 71 and the ion-sensitive FET transducer 1 to contact a buffer solution 61 containing phosphorus acid and having a pH value of 7, and adjusting the voltage $V_{GS}$ between the gate and source of the ion-sensitive FET transducer 1 so that the current Id can exhibit such curves as shown in FIG. 10 at different temperatures, for example, 15° C. and 45° C., the point of intersection of the curves so obtained representing the cancelling current $I_T$.

It is to be noted that the voltage of a power source, shown in Vd in FIG. 9, may not be the same as the drain voltage Vd shown in FIGS. 6 and 8, but may be any value provided that the measurement can be carried out within the saturation region of the ion-sensitive FET transducer 1.

Thus, since the determination of the cancelling current $I_T$ is performed during the determination of static characteristics of the ion-sensitive FET transducer that follow subsequent to the manufacture of such ion-sensitive FET transducer, no extra labor is required in doing so.

Figure 11:
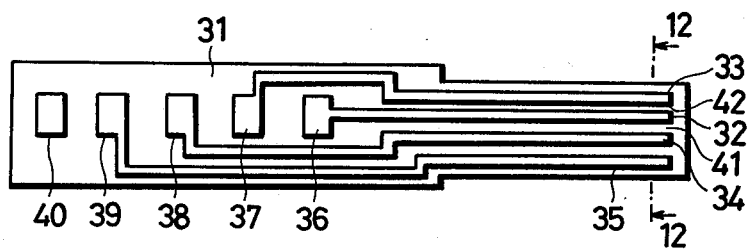
FIG. 11 is a view similar to FIG. 4, showing another type of ion-sensitive FET transducer.

Shown in FIG. 11 is another type of ion-sensitive FET transducer wherein the reference electrode and the ion sensor are incorporated therein as a single integer. The details of the structure of this ion-sensitive FET transducer shown in FIG. 11 is disclosed in the Japanese Patent Laid-open Publication No. 54-81897, published on June 29, 1979, and therefore they are herein omitted for the sake of brevity. However, briefly speaking, this ion-sensitive FET transducer comprises a common silicon substrate 31 having a common diffused n region or common drain 32, separate sources 33 and 34 respectively for the reference electrode and the ion sensor, and separate gate regions 42 and 41 respectively for the reference electrode and the ion sensor, all being formed on said common silicon substrate 31. This silicone substrate 31 also has formed thereon a control electrode 35 for the purpose of maintaining the potential of the electrolyte solution 48 at a constant, controlled value, said control electrode 35 being made of gold and deposited on the silicon substrate 31 by the use of any known metal vapor deposition technique. Reference numerals 36, 37, 38, 39 and 40 represents electrodes electrically connected to and drawn from the common drain 32, the reference electrode source 33, the ion sensor source 34, the control electrode 35 and the silicon substrate 31.

Figure 12:
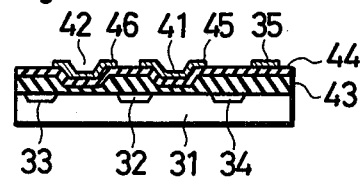
FIG. 12 is a cross sectional view taken along the line 12—12 in FIG. 11.

As can readily be understood from FIG. 12, each of the gate regions 41 and 42 is of a two-layered structure composed of a layer 43 of silicon oxide formed on the silicon substrate 31 and a layer 44 of silicon nitride overlaying the silicon oxide layer 43, and the sensor gate region 41 is covered by, for example, an ion sensitive layer 45 while the gate region 42 of the reference electrode is covered by an organic membrane 46 having a hydrophobic property.

Figure 13:
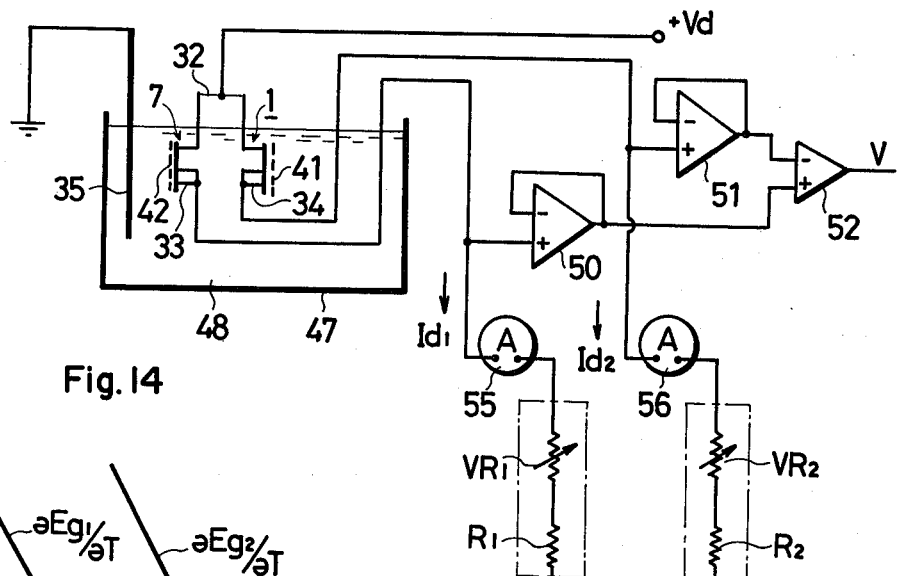
FIG. 13 is a diagram similar to FIG. 2, showing the electric circuitry according to a further preferred embodiment of the present invention.

An electrical equivalent circuit of the ion-sensitive FET transducer of the construction shown in FIGS. 11 and 12 is shown in FIG. 13. As can be understood from FIG. 13, during the measurement of the ion concentration, the ion-sensitive FET transducer or ion sensor 1 is immersed in an electrolyte solution 48 contained in a vessel or container 47 with the common drain layer 32 electrically connected to the constant voltage source $+Vd$ while the source 33 of the reference electrode 7 and the sensor source 34 are electrically respectively connected to impedance converter 50 and 51, so that a difference in output potential between these converters 50 and 51 can be indicated by a substractor circuit 52, an output from the substractor circuit 52 being an indication of the concentration of ions in the electrolyte solution 48.

The measuring circuit shown in FIG. 13 includes current controllers 53 and 54 for controlling the drain currents $I_{d1}$ and $I_{d2}$ flowing the respective source-and-drain paths, and ammeters 55 and 56 inserted respectively between the current controller 53 and the reference electrode source 33 and between the current controller 54 and the sensor source 34 for indicating the actual currents $I_{d1}$ and $I_{d2}$ flowing therethrough.

Figure 14:
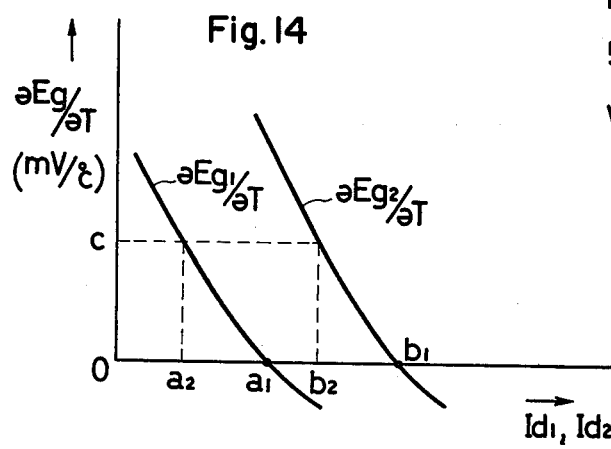
FIG. 14 is a graph showing the temperature dependencies of the different gate potentials relative to the different drain currents.

FIG. 14 illustrates temperature dependencies $\partial Eg1/\partial T$ and $\partial Eg2/\partial T$ of the sum of the gate potentials and the source potentials Eg1 and Eg2 relative to the drain currents $I_{d1}$ and $I_{d2}$ in the gate regions 42 and 41, respectively.

Referring to FIG. 14, when the drain current $I_{d2}$ of the sensor source 34 and the drain current $I_{d1}$ of the reference electrode source 33 are adjusted to values b1 and a1 by manipulating the current controllers 54 and 53, respectively, the temperature dependencies $\partial Eg2/\partial T$ and $\partial Eg1/\partial T$ of the respective sum of the gate potentials and the source potentials Eg1 and Eg2 become zero.

Alternatively, if the drain currents $I_{d1}$ and $I_{d2}$ are adjusted to values $a_2$ and $b_2$ by manipulating the current controllers 53 and 54, respectively, the temperature dependencies of the sum of the gate potentials and the source potentials Eg1 and Eg2 become equal to each other as shown by c in FIG. 14 even though they do not become zero, and therefore, the subtractor circuit 52 can give a potential difference from which the value c has been subtracted. Accordingly, an accurate and precise measurement of the ion concentration in the electrolyte solution 48 can be performed without being adversely affected by change in temperature.

It is to be noted that, if the values $a_1$ and $b_1$ of the source-to-drain currents $I_{d1}$ and $I_{d2}$ are extremely low, noises tend to appear in the measurement system, that is, the SN ratio tends to increase. On the other hand, if the values $a_1$ and $b_1$ of the source-to-drain currents $I_{d1}$ and $I_{d2}$ are extremely high, there will be such possibilities that the living body will be shocked by electric current and get a fever and that the battery providing a source of electric power used in the measurement system will run out in a short period of time. Therefore, the values $a_1$ and $b_1$ of the source-to-drain currents $I_{d1}$ and $I_{d2}$ are preferred to be adjusted within the range of 5 $\mu$A and 1 mA. The range of 20 $\mu$A to 600 $\mu$A is more preferred where the measurement of the ion concentration is subjected to the living body for a prolonged period of time. With respect to the value c, 5 mV/°C. will be usually sufficient, and a large value should be avoided.

Thus, according to the present invention, the ion-sensitive FET transducer may be used during the measurement either with its drain grounded or with its source grounded. However, the use of the transducer with its drain grounded is preferred because, when the transducer is used with its source grounded, the drain current tends to vary during the measurement and, also, the electrical signal does not exhibit a linear relationship with the value being measured, for example, the pH value.

Although the present invention has fully been described in connection with the preferred embodiments thereof with reference to the accompanying drawings, it is to be noted that various changes and modifications are apparent to those skilled in the art. By way of example, the concept of the present invention can equally be applicable to other sensors than the ion sensor, for example, a FET gas sensor selectively sensitive to carbonic acid gas or ammoniac gas as well as a FET enzyme sensor utilizing an enzyme.

Accordingly, such changes and modifications are to be understood as included within the true scope of the present invention as represented by the appended claims unless they depart therefrom.

What is claimed is:

1. A method for measuring the activity of ions in a liquid of interest by the use of a gate-insulated field-effect transistor having a gate electrode, a source electrode and a drain ion sensitive layer with a channel defined between the source and drain, and a reference electrode, which comprises immersing the field-effect transistor and the reference electrode, supplying an electric power to both the field-effect transistor and the reference electrode, and adjusting the drain current flowing through the field-effect transistor to a predetermined value such that the temperature dependency of the electroconductivity of the channel of the field-effect transistor becomes equal to the sum of the temperature dependency of the potential at an interface between the reference electrode and the liquid of interest and the temperature dependency of the potential at an interface between the ion-sensitive layer and the liquid of interest.

2. A method as claimed in claim 1, wherein the adjusting step is carried out by manipulating an current controller for controlling the electric current flowing through the source-and-drain path of the field-effect transistor.

3. An electric circuitry for use in the measurement of the activity of ions in a liquid of interest, which comprises, in combination:
an ion sensor constituted by a gate-insulated field-effect transistor and having a sensor gate, a reference electrode gate and a reference electrode; a substractor circuit for determining a difference in potential between the potential at an interface between the reference electrode and the liquid of interest and the potential at an interface between the sensor gate and the liquid of interest; and a current controller for controlling an electric current flowing through the source-to-drain path of the ion sensor, whereby said current controller may be manipulated to adjust the electric current to a value such that the temperature dependency of the ion sensor relative to the reference electrode becomes equal to the temperature dependency of the reference electrode relative to the reference electrode gate.

4. A circuitry as claimed in claim 3, wherein said current controller comprises a series-connected circuit of variable resistor and fixed resistor.

5. A circuitry as claimed in claim 3, wherein said ion sensor also has a control electrode.

6. A circuitry as claimed in claim 3, 4 or 5, wherein said current controller comprises a series-connected circuit of variable and fixed resistors.

* * * * *